United States Patent
Kucharzyk et al.

(10) Patent No.: US 10,907,143 B2
(45) Date of Patent: Feb. 2, 2021

(54) ENZYME FORMULATION AND METHOD FOR DEGRADATION

(71) Applicant: Battelle Memorial Institute, Columbus, OH (US)

(72) Inventors: Katarzyna Hanna Kucharzyk, Columbus, OH (US); Ramanathan Lalgudi, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 578 days.

(21) Appl. No.: 15/509,283

(22) PCT Filed: Sep. 8, 2015

(86) PCT No.: PCT/US2015/048851
§ 371 (c)(1),
(2) Date: Oct. 18, 2017

(87) PCT Pub. No.: WO2016/040266
PCT Pub. Date: Mar. 17, 2016

(65) Prior Publication Data
US 2018/0142229 A1    May 24, 2018

Related U.S. Application Data

(60) Provisional application No. 62/047,329, filed on Sep. 8, 2014, provisional application No. 62/047,894, filed (Continued)

(51) Int. Cl.
C12N 11/04 (2006.01)
B09C 1/10 (2006.01)
C12N 11/10 (2006.01)

(52) U.S. Cl.
CPC ............... *C12N 11/04* (2013.01); *B09C 1/10* (2013.01); *C12N 11/10* (2013.01);
(Continued)

(58) Field of Classification Search
CPC ........... B09C 1/10; C12N 11/04; C12N 11/10; C12Y 110/03002; C12Y 111/01013; C12Y 111/01014
See application file for complete search history.

(56) References Cited

U.S. PATENT DOCUMENTS 4,554,075 A      11/1985  Chang et al.
5,194,161 A *    3/1993   Heller ............... B01J 35/004
                                              210/748.09
(Continued)

FOREIGN PATENT DOCUMENTS

CN     101845420 A    9/2010
CN     1025800998 A   7/2012
(Continued)

OTHER PUBLICATIONS

Jeffrey K. Glenn, Michael H. Gold, Purification and characterization of an extracellular Mn(II)-dependent peroxidase from the lignin-degrading basidiomycete, Phanerochaete chrysosporium, 1985, Archives of Biochemistry and Biophysics, vol. 242, Issue 2, pp. 329-341 (Abstract only) (Year: 1985).*
(Continued)

*Primary Examiner* — Renee Claytor
*Assistant Examiner* — Trent R Clarke
(74) *Attorney, Agent, or Firm* — Frank Rosenberg; Susanne A. Wilson (57) ABSTRACT

An enzyme formulation includes an encapsulated fungal enzyme which is effective for degrading at least one material selected from the group consisting of hydrocarbons, vulcanized rubber, synthetic rubber, natural rubber, vulcanized polymers and perfluorinated compounds. A degradation method includes treating one of the above-mentioned materials with an encapsulated fungal enzyme to degrade the material.

11 Claims, 3 Drawing Sheets

Related U.S. Application Data on Sep. 9, 2014, provisional application No. 62/198,973, filed on Jul. 3, 2015.

(52) U.S. Cl.
CPC .............. *C12Y 110/03002* (2013.01); *C12Y 111/01013* (2013.01); *C12Y 111/01014* (2013.01)

(56) References Cited

U.S. PATENT DOCUMENTS

| | | | |
|---|---|---|---|
| 5,389,356 A | 2/1995 | Aust et al. | |
| 5,556,779 A | 9/1996 | Khindaria et al. | |
| 6,204,049 B1* | 3/2001 | Bennett | C12N 1/14 424/490 |
| 6,458,387 B1* | 10/2002 | Scott | A61K 9/1635 424/484 |
| 6,541,230 B1 | 4/2003 | Gordon et al. | |
| 6,872,388 B1* | 3/2005 | Lartey | A01N 63/04 424/405 |
| 7,419,593 B2 | 9/2008 | Trauger et al. | |
| 8,919,039 B2 | 12/2014 | Huang et al. | |
| 9,765,324 B2 | 9/2017 | Corgie et al. | |
| 2002/0151038 A1 | 10/2002 | Raghukumar et al. | |
| 2005/0067347 A1* | 3/2005 | Vanhulle | C02F 1/78 210/606 |
| 2011/0278223 A1 | 11/2011 | DeLozier et al. | |

FOREIGN PATENT DOCUMENTS

| | | |
|---|---|---|
| CN | 104722572 A | 6/2015 |
| EP | 1238718 A1 | 9/2002 |
| EP | 2677030 A1 | 12/2013 |
| ES | 2469741 A1 | 6/2014 |
| KR | 100866999 B1 | 11/2008 |
| RU | 2021371 C1 | 10/1994 |
| TW | 201328988 A | 7/2013 |
| WO | 0121332 A1 | 3/2001 |
| WO | 0218551 A2 | 3/2002 |
| WO | 2015094933 A1 | 6/2015 |

OTHER PUBLICATIONS

Don-Hee Park et al., Hydrogen sulfide removal utilizing immobilized *Thiobacillus* sp. IW with Ca-alginate bead, 2002, Biochemical Engineering Journal, vol. 11, pp. 167-173 (Year: 2002).*
Susana Rodriquez Cuoto, Jose Luis Toca Herrera, Industrial and Biotechnological Applications of Laccases: A Review, Biotechnology Advances 24 (2006) 500-513,Tarragona, Spain.
Wang, Yajun and Caruso, Frank, Mesoporous Silica Spheres as Supports for Enzyme Immobilization and Encapsulation, Chem. Mater. 2005, 17, 953-961, Melbourne, Victoria 3010, Australia.
Dominguez, Alberto, Gomez, Jose, Lorenzo, Miriam, Sanroman, Angeles, Enhanced Production of Laccase Activity by Trametes Versicolor Immobilized Into Alginate Beads by the Addition of Different Inducers, World J. Microbiol Biotechnol (2007), 23:367-373, Vigo, Spain.
Dai, Yunrong, Niu, Junfeng, Liu, Jia, Yin, Lifeng, Xu, Jiangjie, In Situ Encapsulation of Laccase in Microfibers by Emulsion Electrospinning: Preparation, Characterization, and Application, Bioresource Technology 101 (2010) 8942-8947, Beijing 100875, PR China.
Faraco, V., Pezzella, C., Miele, A., Giardina, P., Sannia, G., Bio-Remediation of Colored Industrial Wastewaters by the White-Rot Fungi Phanerochaete Chrysosporium and Pleurotus Ostreatus and Their Enzymes, Biodegradation (2009), 20:209-220, Naples, Italy.
Husain, Qayyum, Husain, Maroof, Kulshrestha, Yasha, Remediation and Treatment of Organopollutants Mediated by Peroxidases: A Review, Critical Reviews in Biotechnology, 2009, 29(2): 94-119; Aurora, Colorado, USA.

Mayer, Alfred M., Staples, Richard C., Laccase: New Functions for an Old Enzyme, Phytochemistry 60 (2002) 551-565, Ithaca, NY 14853, USA.
Duran, Nelson, Rosa, Maria A., D'Annibale, Alessandro D., Gianfreda, Liliana, Applications of Laccases and Tyrosinases (Phenoloxidases) Immobilized on Different Supports: A Review, Enzyme and Microbial Technology 31 (2002) 907-931, Napolia, Italy.
Bautista, L. Fernando, Morales, Gabriel, Sanz, Raquel, Immobilization Strategies for Laccase from Trametes Versicolor on Mesostructured Silica Materials and the Application to the Degradation of Naphthalene, Bioresource Technology 101 (2010) 8541-8548 Madrid, Spain.
Hu, Xiaoke, Wang, Pang, Hwang, Huey-Min, Oxidation of Anthracene by Immobilized Laccase from Trametes Versicolor, Bioresource Technology 100 (2009) 4963-4968, Jackson, MS 39217, USA.
Hu, Xiaoke, Zhao, Xueheng, Hwang, Huey-Min, Comparative Study of Immobilized Trametes Versicolor Laccase on Nanoparticles and Kaolinite, Chemosphere 66 (2007) 1618-1626, Jackson, MS 39217, USA.
Lee, Chia-Hung, Lin, Tien-Sung, Mou, Chung-Yuan, Mesoporous Materials for Encapsulating Enzymes, Nano Today (2009) 4, 165-179, St. Louis, MO 63130, USA.
Gassara, Fatma, Brar, Satinder K., Verma, M., Tyagi, R.D., Bisphenol A Degradation in Water by Ligninolytic Enzymes, Chemosphere 92 (2013) 1356-1360, Quebec, Canada GIP 3W8.
Acevado, F., Pizzul, L., Castillo, M.dP., Gonzalez, M.E., Cea, M., Gianfreda, L., Diez, M.C., Degradation of Polycyclic Aromatic Hydrocarbons by Free and Nanoclay-Immobilized Manganese Peroxides from Anthracophyllum Discolor, Chemosphere 80 (2010) 271-278, Uppsala, Sweden.
Spulber, Mariana, Baumann, Patric, Saxer, Sina S., Pieles, Uwe, Meier, Wolfgang, Bruns, Nico, Poly(N-vinylpyrrolidone)-Poly(dimethylsiloxane)-Based Polymersome Nanoreactors for Laccase-Catalyzed Biotransformations, Biomacromolecules, 15, (2014) 1469-1475, Basel, Switzerland.
Xiao, Pengfei, et al., Biotransformation of the organochlorine pesticide trans-chlordane by wood-rot fungi, New Biotechnology, vol. 29, No. 1, pp. 107-115, Dec. 2011.
Nyakundi W.O. et al., Biodegradation of Diazinon and Methomyl Pesticides by White Rot Fungi from Selected Horticultural Farms in Rift Valley and Central Kenya, Journal of Applied Technology in Environmental Santiation, vol. 1, No. 2: 107-124, Aug. 2011.
Bending, Gary D. et al., Degradation of contrasting pesticides by white rot fungi and its relationship with ligninolytic potential, FEMS Microbiology Letters 212 (2002) 59-63.
Fragoeiro, Silvia, et al., Impact of Trametes versicolor and Phanerochaete chrysoporium on differential breakdown of pesticide mixtures in soil microcosms at two water potentials and associated respiration and enzyme activity, International Biodeterioration & Biodegradation, vol. 62, Issue 4, Dec. 2008, pp. 376-383.
Pizzul, Leticia, et al., Degradation of glyphosate and other pesticides by ligninolytic enzymes, Biodegradation (2009) 20:751-759.
Lynch, James, Excerpts from Biotechnology Research Series: 6, Bioremediation: Principles and Applications, Cambridge University Press, 1996 pp. 135, 141-143.
Young, Darcy, et al., Degradation of Bunker C Fuel Oil by White-Rot Fungi in Sawdust Cultures Suggests Potential Applications in Bioremediation, PLOS One, DOI: 10.1371, Jun. 25, 2015.
Bogan, Bill W. et al., Polycyclic Aromatic Hydrocarbon-Degrading Capabilities of Phanerochaete laevis HHB-1625 and Its Extracellular Ligninolytic Enzymes, Applied and Enviromental Microbiology, May, 1996, p. 1597-1603, vol. 62, No. 5.
Bamforth, Selina, et al., Review Bioremediation of polycyclic aromatic hydrocarbons: current knowledge and future directions, J. Chem. Technol 80: 723-736 (2005).
Perullini, Mercedes, et al., Alginate/porous silica matrices for the encapsulation of living organisms: tunable properties for biosensors, modular bioreactors, and bioremediation devices, Mesoporous Biomater., 2015, 2:3-12.
Taboada-Puig, R., et al., Combined cross-linked enzyme aggregates from versatile peroxidase and glucose oxidase: Production, partial characterization and application for the elimination of endocrine disruptors, Bioresource Technology 102 (2011) 6593-6599.

(56) References Cited

OTHER PUBLICATIONS

Xie, Han, et al., Fabrication of a novel immobilization system and its application for removal of anthracene from soil, Biochemical Engineering Journal 97 (2015) 8-16.

* cited by examiner

ENZYME FORMULATION AND METHOD FOR DEGRADATION

CROSS-REFERENCE TO RELATED APPLICATIONS

This is a national stage application filed under 35 USC § 371 of international application PCT/US2015/048851 filed Sep. 8, 2015, which claims the priority to U.S. Provisional Applications Ser. No. 62/047,329 filed Sep. 8, 2014; Ser. No. 62/047,894 filed Sep. 9, 2014; and Ser. No. 62/198,973 filed Jul. 30, 2015, the entire disclosures of which are expressly incorporated herein by reference.

BACKGROUND OF THE INVENTION

Hydrocarbon contamination resulting from drilling and extraction of oil has become one of the major environmental problems. Accidental releases of petroleum products are of particular concern for human health since hydrocarbon components cause extensive damage to the environment and contaminate the soil. The microbially mediated breakdown of heavy weathered total petroleum hydrocarbons (TPH) has its limitations due to the degradation of only up to 4-ring aromatic compounds and 25-carbon saturated compounds. Moreover, the presence of polycyclic aromatic hydrocarbons (PAHs) with two or more fused benzene rings in linear, angular or cluster structural arrangements and low solubility poses an additional remediation challenge.

Therefore, it would be desirable to provide a new enzyme formulation and method for enhanced degradation of hydrocarbons. The enzyme formulation can be particularly useful for enhanced remediation of hydrocarbon contaminated soil matrices.

It would also be desirable to provide an enzyme formulation and method for the degradation of vulcanized rubber, synthetic rubber, natural rubber, vulcanized polymers and perfluorinated compounds.

SUMMARY OF THE INVENTION

An enzyme formulation comprises an encapsulated fungal enzyme which is effective for degrading at least one material selected from the group consisting of hydrocarbons, vulcanized rubber, synthetic rubber, natural rubber, vulcanized polymers and perfluorinated compounds.

A degradation method comprises treating one of the above-mentioned materials with an encapsulated fungal enzyme to degrade the material.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

Figure 1:
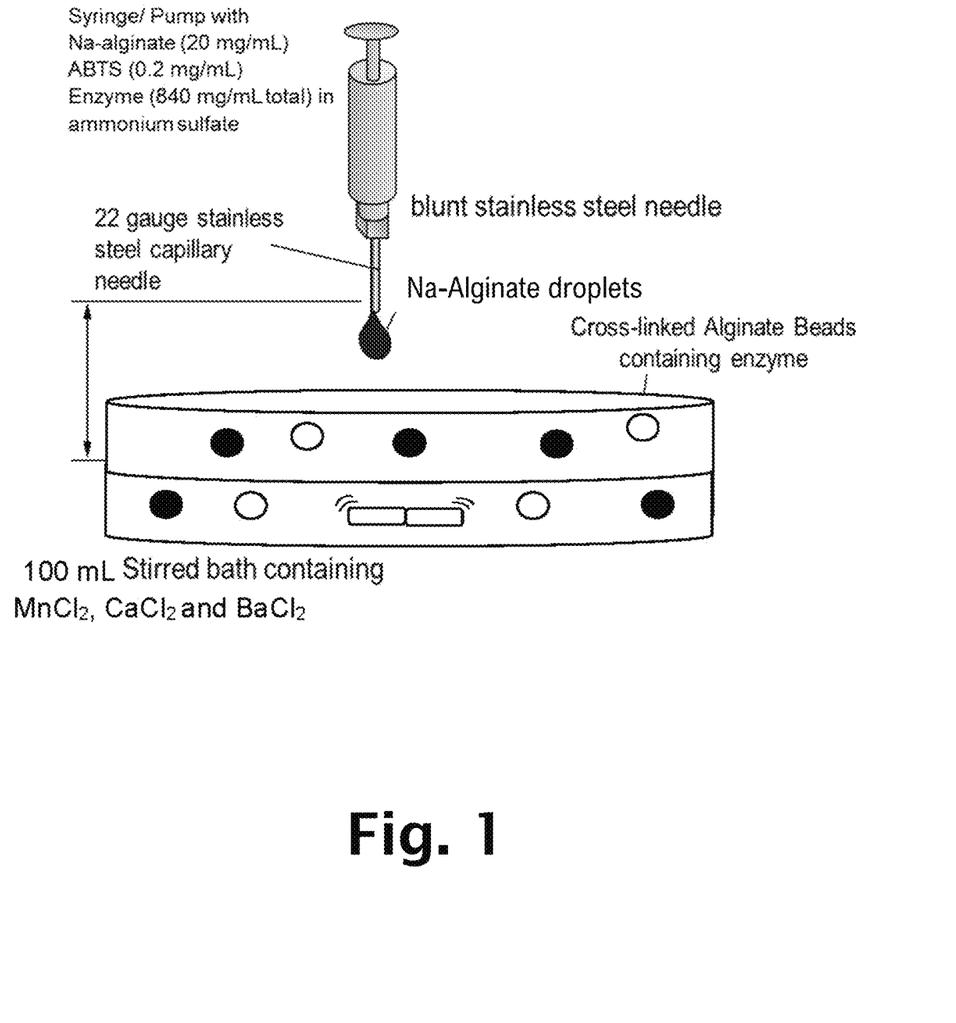
FIG. 1 illustrates the experimental setup for alginate encapsulation of enzyme.

FIG. 1. Illustration of the experimental set up for alginate encapsulation of enzyme.

DETAILED DESCRIPTION OF THE PREFERRED EMBODIMENTS

The ability of ligninolytic enzymes to degrade larger molecular compounds through the use of radical reactions brings potential to enhance the degradation of crude oil and other hydrocarbons. Since ligninolytic enzymes are extracellular, they are able to diffuse effectively to the highly immobile high molecular weight hydrocarbons and result in metabolites that are more bioavailable for further microbially induced breakdown.

The present invention includes ligninolytic enzymes which are encapsulated to stabilize the enzymes. The invention can further include formulating the stabilized enzymes for a specified application such as for the breakdown of TPHs.

The invention can further include the encapsulation of other species of fungal enzymes for use in breaking down other materials.

Example of Process for Producing Ligninolytic Enzymes:

Fungal species of, but not limited to, *Phanaerochete chrysosporium, Nematoloma forwardii* or *Trametes versicolor* are cultivated in flask and bioreactor cultures in standard conditions. Other examples of fungal species and known producers of ligninolytic enzymes include *Phanerachete* spp, *Tremetes* spp, *Phlebia* spp, *Cerena* spp, *Merulius* spp, *Pellinius* spp, *Cyatus* spp, and *Stereum* spp. The selected fungus secretes extracellularly into the growth medium a suite of ligninolytic enzymes: manganese peroxidase, lignin peroxidase and laccase. The enzyme activity can be analyzed using standard methods.

The use of purified enzyme results in the highest possible activity. Once the activities of manganese peroxidase and lignin peroxidase reach maximum, the extracellular liquids with growth medium are collected. The fungal mycelium is separated from the liquid components via sterile gauze and incinerated. The remainder of extracellular liquids is then filtered and purified using standard methods. Purified enzyme suite is then lyophilized and utilized for further stabilization.

Any suitable ligninolytic enzyme(s) can be used in the invention. The major groups of ligninolytic enzymes include lignin peroxidases, manganese peroxidases, versatile peroxidases, and laccases, examples of which are known to enzyme scientists.

Although the enzymes may be a suite of enzymes produced by a fungus, alternatively a single type of ligninolytic enzyme may be used. Further, the enzyme(s) are not necessarily produced by a fungus, but could instead be produced by a microorganism or other source. Although purified enzymes are preferred, in certain embodiments the enzymes may be used in nonpurified form.

Enzymes Stabilization:

The enzymes are stabilized by encapsulation. For example, the enzymes can be encapsulated in a protective shell. In certain embodiments, the type of encapsulation is microencapsulation. The shell can be any material that is effective to stabilize the enzymes. In certain embodiments, the shell is effective to cause slow release of the enzymes. For example, in one enzyme release experiment the encapsulated enzymes had a very low enzyme activity the first 7 days, and the enzyme activity gradually increased to a high activity between days 7 and 28.

In certain embodiments, the shell consists of a crosslinked hydrogel. Crosslinking is a way of curing the hydrogel. The process of crosslinking initiates from the outer layer and progresses to the core; in this way the enzymes are forced to stay inside the hydrogel. Furthermore, the crosslinking reaction provides rigidity to the hydrogel. It is also believed that a crosslinker such as manganese will get involved into the enzyme catalytic cycle and replenish manganese as needed during the decontamination process.

The cross-linked hydrogel is exemplified by but not limited to calcium alginate, manganese alginate, zirconium alginate, calcium poly(aspartate), manganese poly(aspartate) and zirconium poly (aspartate).

More generally, a good match of the encapsulating (shell) material and the enzymes may be determined based on the concentration, and the valency of the cation. For example, higher concentration and higher valent cation (Zr+4 is more effective than Ca+2) increases the gelation time.

In another embodiment the enzymes are stabilized by encapsulation in a shell having two or more layers. For example, the protective shell may comprise two layers wherein the first layer interfaced with the enzyme is a cross-linked hydrogel, and the second layer interfaced with the first layer is a hydrophobic material such as an oleogel. The two layer shell is for swelling the contaminants in the outermost layer followed by oxidation reaction in the inner layer when they come in contact with the enzyme. The hydrophobic material can attract and be attracted to hydrocarbons.

The oleogel is exemplified by but not limited to poly (lauryl methacrylate), poly(stearyl methacrylate), poly(isoprene) and poly (butadiene).

In certain embodiments, the encapsulant has one or more of the following benefits: room temperature process, bio-based and biodegradable matrix, absorbs water, fast synthesis, VOC free/no solvents, variable particle size, and stable pH 4 to 6 range.

In certain embodiments, the shell works as a donor of one or more mediators for activation of enzymes within the capsule. For example, as described above, a manganese crosslinker can replenish manganese to activate the enzyme catalytic cycle. In certain embodiments, the shell is formulated to attract oil molecules or other material to be degraded.

The encapsulated enzymes can be produced in the form of beads or any other form suitable for a particular application. In certain embodiments, the beads have a diameter within a range of from about 1.5 mm to about 5 mm, and more particularly within a range of from about 2.8 mm to about 3.5 mm ("diameter" refers to maximum diameter). In several examples, ligninolytic enzymes have been encapsulated in an alginate shell to produce spherical beads having diameters of 1.9 mm, 2.8 mm and 3.0 mm.

Example

The process of stabilizing the enzyme is further exemplified in the following example. 10 mg of manganese peroxidase was rinsed into 10 g of alginate stock solution with 1 mL of deionized water. The suspension was mixed until dissolve with vial mixer and uniform. 10 grams of alginate mixture was then drawn up into a 10 mL syringe. Alginate drops containing manganese peroxidase were dropped using 0.3 mm gauge needle into the 50 mL calcium chloride solution using syringe pump (Cole-Palmer 78-0100C) with the retention time of 100 mL/h. Formation of encapsulated gel-like beads of alginate-enzyme complex was detected. The enzyme capsules were then left to settle at the bottom of the container and refrigerated at 8 C until use.

Formulating the Stabilized Enzyme for a Specified Application:

The invention further includes formulating the stabilized enzyme for specified application. In one example, the stabilized enzyme is formulated in a liquid or solid matrix. The matrix comprises a peroxide such as hydrogen peroxide or its derivatives and dispersing aid such as surfactants.

Possible Market and Product Applications:

Encapsulated fungal enzymes in the environmental setting for the purpose of degradation of total petroleum hydrocarbons may be of interest to oil and gas companies. Furthermore, since radical reaction pathway of fungal ligninolytic enzymes is highly unspecific, the application of the technology may be broad ranging from: degradation of heavily weathered petroleum hydrocarbons, petroleum hydrocarbons, jet fuel, Navy special fuel, polyfluorinated compounds (PFCs), dioxins; PCBs, herbicides, pesticides, munition constituents, lubricants, oils, detoxification of industrial effluents, and dye effluents. The enzyme formulation and method can be useful for the degradation of vulcanized rubber, synthetic rubber, natural rubber, vulcanized polymers and perfluorinated compounds such as perfluorooctanesulfonic acid and perfluorooctane sulfonate.

Evaluation of Fungal Enzyme Extracts to Catalyze Remediation of Heavily Weather Crude Oil Contaminated Soil:

Objective: To develop a method to treat heavily weathered crude contaminated soil to <1% TPH encapsulated fungal enzymes.

Hypothesis: Fungal enzymes can non-selectively break down long-chain hydrocarbons into shorter chain hydrocarbons that can be further degraded by microorganisms.

*Phanerochaete chrysosporium*

Secrete a suite of oxidoreductases (manganese peroxidase, laccase and lignin peroxidase).

Figure 2:
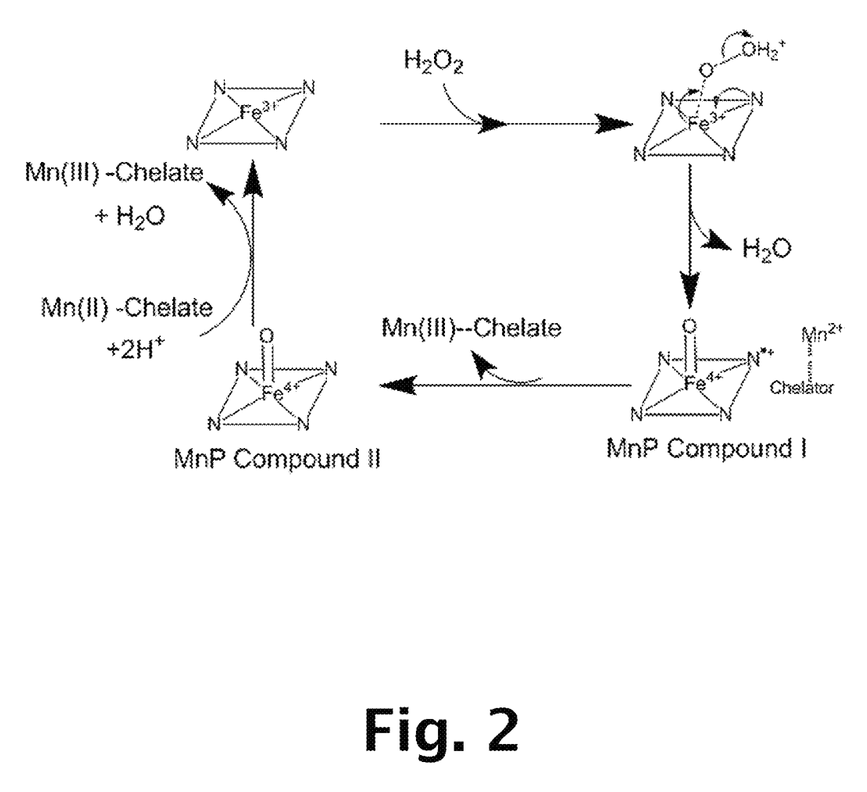
FIG. 2 illustrates the reaction pathways of heme porphyrin with various reactants.
Figure 3:
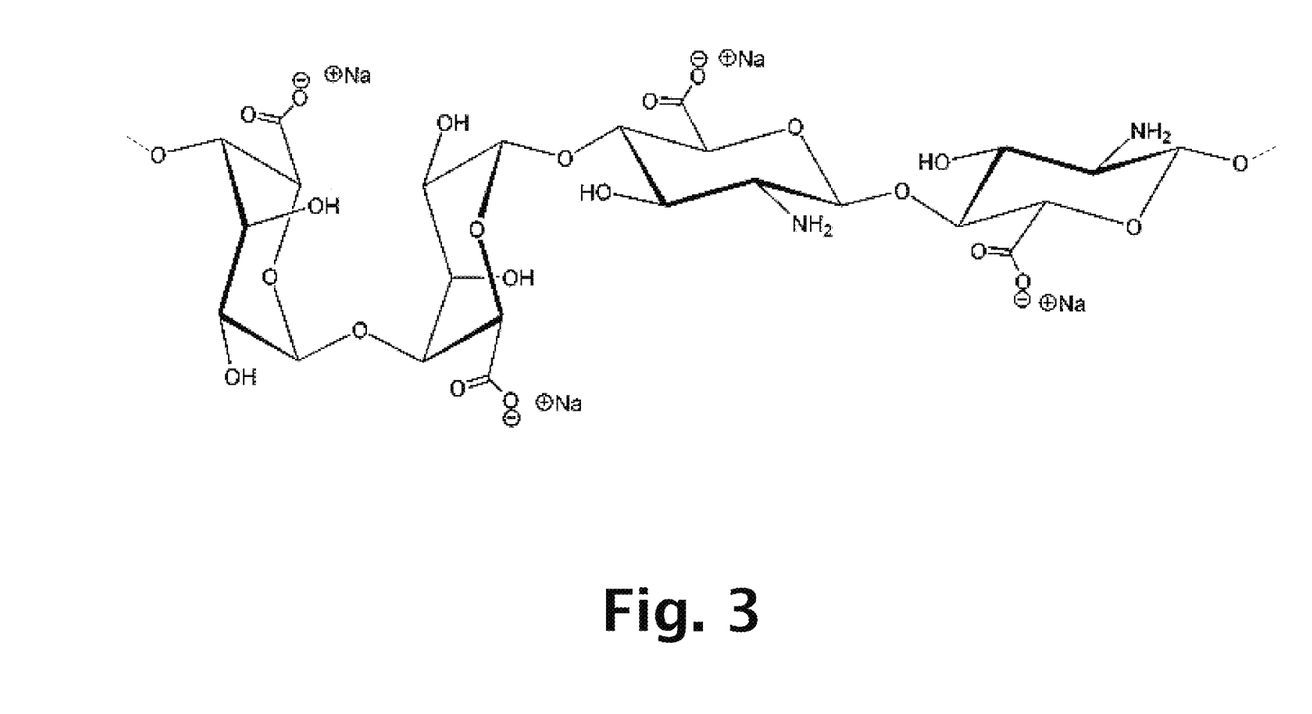
FIG. 3 illustrates the molecular structure of a tetrasaccharide monomer of the ionotropic alginate ion polymer.

The cation radical of heme porphyrin reacts with an array of compounds and initiates non specific of recalcitrant environmental pollutants.(See FIG. 2).

Enzyme Characteristics:

Non specific degradation of recalcitrant environmental pollutants e.g. TPH.

Dosage for treating recalcitrant contaminants—1 U/1.89 mg/kg PAH.

Encapsulation:

To provide reactive ingredient (enzyme) in an easily applicable form without the risk of introducing non native fungal species.

Examples of Encapsulation Technology:

Microencapsulation via spray drying with mixture of polymer and solvent (solid material)

Encapsulation into hydrogel particles using non aqueous dispersion process

Encapsulation using complex co-aservation

Encapsulation via electrospray

Selection of Encapsulant:

Match suitable encapsulation route with critical process metrics to gain high probability of success.

Ionotropic alginate gellation benefits:

Room temperature process

Bio-based and biodegradable matrix

100% aqueous

Fast process

VOC free/No solvents

Variable particle size

Contaminated Samples:

Grand Calumet River Sediments

Contamination from multiple industries including oil refineries on the banks of the river Contamination in place since 1970's Contaminants include PCBs, heavy metals, crude oil, PAHs, heavily weathered petroleum hydrocarbons, petroleum hydrocarbons, vulcanized rubber, jet fuel, Navy special fuel, synthetic rubber, polyfluorinated compounds (PFCs), dioxanes; PCBs, herbicides, pesticides, and munition constituents.

Soil Characteristics

| | Concentration (mg/kg dry weight) |
|---|---|
| TPH in Soil | |
| C6-C12 | ND |
| >C12-C28 | 1,530 |
| >C28-C35 | 581 |
| Total C6-C35 | 2,110 |
| PAHs in Soil | |
| Acenaphthene | 0.231 |
| Acenaphthylene | 1.45 |
| Benzo[a]anthracene | 9.78 |
| Chrysene | 31.6 |
| Phenanthrene | 19.1 |
| Fluoranthene | 15.31 |

Soil Moisture Content 17%

Metagenomics and Metaproteomics:
To understand the shift in microbial population as a result of application of fungal enzymes and degradation of TPH
To detect suite of microbial proteins directly involved in TPH degradation
Use data to optimize treatment
Application of Omic Technologies:
Biodegradation:
Baseline and time/dose response characterization
Community structure (microbes)
Functional potential (genes)
Function (proteins)
Additional Work:
Optimize encapsulation conditions
Conduct experiment with encapsulated enzyme formulation
Analysis of metaproteome after treatment with encapsulated enzyme to compare protein composition
Application to Field Treatment:
Formulation of encapsulated enzyme with hydrogen peroxide embedded
Apply encapsulated enzyme into vadose zone soils using backhoe
Encapsulant is resistant to mechanical stress due to size
Reaction is expected to occur rapidly with the reduction in TPH seen within 28-30 days after application
Measure TPH concentration to determine when to reapply enzyme

EXPERIMENTATION

Laboratory Experiment Approach:
Dry Soil
Grow culture of *P. chrysosporium* and collect extracellular enzyme extract
Lyophilize enzyme extract and resuspend in 10 ML
Apply to soil microcosm and add hydrogen peroxide (reaction substrate)
pH 4.5, Temp 25 C Treatments

| Set Up | Soil | Enzyme | Peroxide |
|---|---|---|---|
| 1 | ✓ | | |
| 2 | ✓ | ✓ | |
| 3 | ✓ | ✓ | ✓ |

20 g soil
2 mL purified enzyme at 20 U/mL
100 µL 10 mM hydrogen peroxide added every other day
TPH and PAH measured after 7 days and 14 days
All treatments prepared in duplicates Results—Soil, Enzymes+$H_2O_2$, Day 7

| | Day 0 (mg/kg dry weight) | Day 7 (mg/kg dry weight) | Percent Loss |
|---|---|---|---|
| TPH in Soil | | | |
| C6-C12 | ND | | |
| >C12-C28 | 1,530 | | |
| >C28-C35 | 581 | | |
| Total C6-C35 | 2,110 | | |
| PAHs in Soil | | | |
| Acenaphthene | 0.231 | | |
| Acenaphthylene | 1.45 | | |
| Benzo[a]anthracene | 9.78 | | |
| Chrysene | 31.6 | | |
| Phenanthrene | 19.1 | | |
| Fluoranthene | 15.31 | | |

ADDITIONAL EXPERIMENTS

1. Selection of Fungal Strains for Production of High Concentrations of Enzymes: Manganese Peroxidase and Laccase.

Exp. 1. *Phanerachaete chrysosporium* 1309, *Lenzites betulina* 141, *Trametes versicolor* 159, *Trametes cervina* 33, *Trametes ochraceae* 1009, *Trametes pubescens* 11, *Stereum hirsutum* 42, *Trametes zonatus* 540, *Trametes hirsuta* 119, *Phlebia radiata* 312.

Composition of synthetic medium, (g/l): $KH_2PO_4$-1.0; $MgSO_4$-0.5; $CaCl_2$-0.1; $FeSO_{4x}7H_2O$-0.005; peptone-2.0; yeast extract-2.0; glycerol-10.0; veratryl alcohol-0.3, pH 5.0.

| | Laccase, U $1^{-1}$ | | | | pH | | | |
|---|---|---|---|---|---|---|---|---|
| | Cultivation days | | | | | | | |
| | 4 | 6 | 8 | 11 | 4 | 6 | 8 | 11 |
| *P. chrysosporium* 1309 | 0 | 0 | 0 | 0 | 5.0 | 6.4 | 6.5 | 6.5 |
| *L. betulina* 141 | 0 | 0 | 0 | 0 | 6.0 | 6.5 | 7.1 | 7.0 |
| *T. versicolor* 159 | 2352 | 890 | 613 | 0 | 6.2 | 7.3 | 6.7 | 6.4 |
| *T. cervina* 33 | 0 | 0 | 0 | 0 | 6.2 | 5.8 | 5.6 | 6.7 |
| *T. ochraceae* 1009 | 121 | 252 | 231 | 111 | 6.0 | 5.9 | 6.1 | 6.0 |
| *T. pubescens* 11 | 0 | 8 | 3 | 0 | 5.9 | 5.0 | 5.7 | 6.0 |
| *S. hirsutum* 42 | 3 | 0 | 0 | 0 | 5.0 | 5.0 | 5.0 | 5.0 |

-continued

| | Laccase, U l$^{-1}$ | | | | pH | | | |
|---|---|---|---|---|---|---|---|---|
| | Cultivation days | | | | | | | |
| | 4 | 6 | 8 | 11 | 4 | 6 | 8 | 11 |
| T. zonatus 540 | 4200 | 3276 | 2394 | 2100 | 5.8 | 6.2 | 6.8 | 6.6 |
| T. hirsuta 119 | 256 | 143 | 336 | 806 | 4.8 | 4.3 | 6.0 | 5.5 |
| P. radiata 312 | 17 | 8 | 10 | 15 | 6.1 | 5.8 | 5.8 | 5.3 |

| | MnP, U l$^{-1}$ (610 nm) | | | | MnP, U l$^{-1}$ (270 nm) | | | |
|---|---|---|---|---|---|---|---|---|
| | Cultivation days | | | | | | | |
| | 4 | 6 | 8 | 11 | 4 | 6 | 8 | 11 |
| P. chrysosporium 1309 | 0 | 0 | 0 | 0 | 0 | 103 | 43 | 0 |
| L. betulina 141 | 0 | 0 | 0 | 0 | 0 | 0 | 0 | 9 |
| T. versicolor 159 | 77 | 890 | 16 | 0 | 99 | 60 | 21 | 0 |
| T. cervina 33 | 59 | 0 | 559 | 254 | 21 | 125 | 168 | 236 |
| T. ochraceae 1009 | 48 | 252 | 205 | 87 | 176 | 280 | 267 | 232 |
| T. pubescens 11 | 0 | 8 | 0 | 0 | 0 | 0 | 0 | 0 |
| S. hirsutum 42 | 0 | 0 | 0 | 0 | 0 | 9 | 9 | 13 |
| T. zonatus 540 | 86 | 3276 | 144 | 100 | 146 | 112 | 99 | 86 |
| T. hirsuta 119 | 0 | 143 | 0 | 0 | 13 | 9 | 9 | 17 |
| P. radiata 312 | 0 | 8 | 0 | 0 | 0 | 9 | 0 | 0 |

| | LiP, U l$^{-1}$ | | | |
|---|---|---|---|---|
| | Cultivation days | | | |
| | 4 | 6 | 8 | 11 |
| P. chrysosporium 1309 | 2 | 6 | 3 | 3 |
| L. betulina 141 | 1 | 2 | 2 | 4 |
| T. versicolor 159 | 9 | 4 | 2 | 2 |
| T. cervina 33 | 1 | 1 | 3 | 6 |
| T. ochraceae 1009 | 4 | 6 | 19 | 19 |
| T. pubescens 11 | 2 | 1 | 8 | 2 |
| S. hirsutum 42 | 0 | 0 | 1 | 1 |
| T. zonatus 540 | 2 | 7 | 14 | 25 |
| T. hirsuta 119 | 6 | 5 | 1 | 3 |
| P. radiata 312 | 9 | 13 | 5 | 8 |

Composition of medium, (g/l): KH$_2$PO$_4$-1.0; MgSO$_4$-0.5; CaCl$_2$-0.1; FeSO$_{4x}$7H$_2$O-0.005; peptone-1.0; yeast extract-2.0; veratryl alcohol-0.3; MP-40.0. pH 5.0.

| | Laccase, U l$^{-1}$ | | | | pH | | | |
|---|---|---|---|---|---|---|---|---|
| | Cultivation days | | | | | | | |
| | 4 | 6 | 8 | 11 | 4 | 6 | 8 | 11 |
| P. chrysosporium 1309 | 0 | 0 | 0 | 0 | 4.2 | 5.8 | 6.8 | 7.4 |
| L. betulina 141 | 0 | 0 | 0 | 0 | 5.8 | 6.0 | 6.4 | 6.5 |
| T. versicolor 159 | 106 | 143 | 235 | 0 | 5.1 | 6.2 | 6.1 | 6.0 |
| T. cervina 33 | 0 | 0 | 0 | 0 | 5.2 | 5.4 | 6.2 | 6.3 |
| T. ochraceae 1009 | 5544 | 5432 | 1596 | 722 | 3.2 | 5.0 | 5.2 | 5.6 |
| T. pubescens 11 | 0 | 0 | 0 | 0 | 5.3 | 5.0 | 5.4 | 4.7 |
| S. hirsutum 42 | 168 | 223 | 164 | 69 | 4.0 | 4.9 | 4.7 | 5.0 |
| T. zonatus 540 | 8400 | 7896 | 5796 | 2520 | 3.8 | 5.2 | 5.2 | 5.7 |
| T. hirsuta 119 | 1276 | 353 | 67 | 22 | 4.0 | 4.6 | 4.3 | 4.0 |
| P. radiata 312 | 0 | 0 | 0 | 0 | 5.0 | 5.1 | 5.6 | 4.2 |

| | MnP, U l$^{-1}$ (610 nm) | | | | MnP, U l$^{-1}$ (270 nm) | | | |
|---|---|---|---|---|---|---|---|---|
| | Cultivation days | | | | | | | |
| | 4 | 6 | 8 | 11 | 4 | 6 | 8 | 11 |
| P. chrysosporium 1309 | 0 | 0 | 0 | 0 | 0 | 0 | 0 | 0 |
| L. betulina 141 | 0 | 0 | 0 | 0 | 17 | 0 | 0 | 13 |
| T. versicolor 159 | 0 | 0 | 0 | 0 | 9 | 9 | 0 | 9 |
| T. cervina 33 | 46 | 966 | 846 | 742 | 0 | 615 | 512 | 396 |
| T. ochraceae 1009 | 100 | 164 | 171 | 104 | 374 | 318 | 310 | 387 |
| T. pubescens 11 | 0 | 0 | 0 | 0 | 0 | 0 | 0 | 0 |
| S. hirsutum 42 | 0 | 0 | 0 | 0 | 17 | 17 | 0 | 0 |
| T. zonatus 540 | 129 | 103 | 97 | 99 | 129 | 215 | 159 | 172 |
| T. hirsuta 119 | 0 | 0 | 0 | 0 | 30 | 9 | 26 | 0 |
| P. radiata 312 | 0 | 0 | 0 | 0 | 0 | 0 | 0 | 4 |

| | LiP, U l$^{-1}$ | | | |
|---|---|---|---|---|
| | Cultivation days | | | |
| | 4 | 6 | 8 | 11 |
| P. chrysosporium 1309 | 192 | 0 | 7 | 0 |
| L. betulina 141 | 0 | 0 | 0 | 11 |
| T. versicolor 159 | 0 | 15 | 37 | 15 |
| T. cervina 33 | 0 | 0 | 0 | 0 |
| T. ochraceae 1009 | 24 | 8 | 14 | 76 |
| T. pubescens 11 | 0 | 0 | 0 | 3 |
| S. hirsutum 42 | 0 | 2 | 1 | 38 |
| T. zonatus 540 | 27 | 16 | 20 | 55 |
| T. hirsuta 119 | 21 | 18 | 14 | 22 |
| P. radiata 312 | 0 | 0 | 0 | 11 |

Exp. 2. Cerrena unicolor 300, Cerrena unicolor 301, Cerrena unicolor 302, Cerrena unicolor 303, Cerrena unicolor 305, Coriolopsis gallica 142, Merulius tremelosus 206, Pellinus tuberculosus 121, Pellinus tuberculosus 131, Cyatus striatus 978.

Composition of synthetic medium, (g/l): KH$_2$PO$_4$-1.0; MgSO$_4$-0.5; CaCl$_2$-0.1; FeSO$_{4x}$7H$_2$O-0.005; peptone-2.0; yeast extract-2.0; glycerol-10.0; veratrylalcohol-0.3, pH 5.0.

| | Laccase, U l$^{-1}$ | | | | pH | | | |
|---|---|---|---|---|---|---|---|---|
| | Cultivation days | | | | | | | |
| | 5 | 7 | 9 | 12 | 5 | 7 | 9 | 12 |
| C. unicolor 300 | 336 | 468 | 286 | 798 | 6.0 | 6.1 | 6.2 | 6.1 |
| C. unicolor 301 | 77 | 134 | 69 | 185 | 5.0 | 5.2 | 5.3 | 5.8 |
| C. unicolor 302 | 172 | 840 | 1260 | 7644 | 5.8 | 5.8 | 6.0 | 6.0 |
| C. unicolor 303 | 76 | 151 | 133 | 407 | 5.3 | 5.8 | 5.4 | 5.8 |
| C. unicolor 305 | 1025 | 420 | 176 | 210 | 5.5 | 5.5 | 5.5 | 5.7 |
| C. gallica 142 | 105 | 332 | 470 | 504 | 5.3 | 5.7 | 5.6 | 5.7 |
| M. tremelosus 206 | 605 | 504 | 181 | 66 | 4.9 | 4.3 | 4.5 | 4.5 |
| P. tuberculosus 121 | 4 | 20 | 0 | 17 | 5.8 | 6.2 | 6.1 | 6.1 |
| P. tuberculosus 131 | 0 | 0 | 2 | 8 | 6.0 | 6.2 | 6.0 | 6.0 |
| C. striatus 978 | 4 | 0 | 0 | 20 | 6.1 | 6.1 | 6.1 | 5.8 |

| | MnP, U l$^{-1}$ (610 nm) | | | | MnP, U l$^{-1}$ (270 nm) | | | |
|---|---|---|---|---|---|---|---|---|
| | Cultivation days | | | | | | | |
| | 5 | 7 | 9 | 12 | 5 | 7 | 9 | 12 |
| C. unicolor 300 | 437 | 79 | 67 | 42 | 645 | 17 | 0 | 0 |
| C. unicolor 301 | 156 | 221 | 552 | 81 | 206 | 482 | 507 | 155 |
| C. unicolor 302 | 34 | 40 | 41 | 70 | 52 | 43 | 26 | 0 |
| C. unicolor 303 | 394 | 734 | 874 | 55 | 507 | 1015 | 576 | 95 |

-continued

| | MnP, U l$^{-1}$ (610 nm) | | | | MnP, U l$^{-1}$ (270 nm) | | | |
|---|---|---|---|---|---|---|---|---|
| | Cultivation days | | | | | | | |
| | 5 | 7 | 9 | 12 | 5 | 7 | 9 | 12 |
| C. unicolor 305 | 206 | 225 | 101 | 49 | 284 | 507 | 215 | 146 |
| C. gallica 142 | 29 | 59 | 22 | 3 | 26 | 17 | 34 | 30 |
| M. tremelosus 206 | 4 | 0 | 0 | 0 | 0 | 0 | 9 | 0 |
| P. tuberculosus 121 | 22 | 56 | 152 | 160 | 0 | 0 | 0 | 0 |
| P. tuberculosus 131 | 119 | 201 | 308 | 128 | 0 | 0 | 0 | 0 |
| C. striatus 978 | 44 | 5 | 0 | 0 | 0 | 0 | 0 | 0 |

| | LiP, U l$^{-1}$ | | | |
|---|---|---|---|---|
| | Cultivation days | | | |
| | 5 | 7 | 9 | 12 |
| C. unicolor 300 | 1 | 2 | 3 | 0 |
| C. unicolor 301 | 0 | 2 | 2 | 15 |
| C. unicolor 302 | 4 | 3 | 2 | 0 |
| C. unicolor 303 | 5 | 18 | 0 | 9 |
| C. unicolor 305 | 1 | 4 | 1 | 30 |
| C. gallica 142 | 9 | 12 | 12 | 3 |
| M. tremelosus 206 | 0 | 0 | 0 | 0 |
| P. tuberculosus 121 | 0 | 0 | 0 | 0 |
| P. tuberculosus 131 | 0 | 0 | 0 | 0 |
| C. striatus 978 | 0 | 0 | 4 | 0 |

Composition of medium, (g/l): $KH_2PO_4$-1.0; $MgSO_4$-0.5; $CaCl_2$-0.1; $FeSO_{4x}7H_2O$-0.005; peptone-1.0; yeast extract-2.0; veratryl alcohol-0.3; glycerol-10.0; MP-20.0. pH 5.0.

| | Laccase, U l$^{-1}$ | | | | pH | | | |
|---|---|---|---|---|---|---|---|---|
| | Cultivation days | | | | | | | |
| | 5 | 7 | 9 | 12 | 5 | 7 | 9 | 12 |
| C. unicolor 300 | 7392 | 6888 | 3654 | 9576 | 5.5 | 5.6 | 5.6 | 5.8 |
| C. unicolor 301 | 4508 | 6552 | 2394 | 4620 | 4.7 | 4.8 | 5.0 | 5.0 |
| C. unicolor 302 | 4620 | 7560 | 5516 | 12432 | 4.6 | 5.7 | 5.8 | 6.0 |
| C. unicolor 303 | 2520 | 4340 | 2520 | 2016 | 4.3 | 5.0 | 5.0 | 5.2 |
| C. unicolor 305 | 4620 | 5992 | 3276 | 5460 | 4.9 | 4.9 | 5.0 | 5.0 |
| C. gallica 142 | 3528 | 2898 | 5292 | 2688 | 4.8 | 5.7 | 5.2 | 5.2 |
| M. tremelosus 206 | 2982 | 3318 | 3570 | 3864 | 4.4 | 4.5 | 4.5 | 4.5 |
| P. tuberculosus 121 | 13 | 42 | 34 | 121 | 4.7 | 5.6 | 5.5 | 5.7 |
| P. tuberculosus 131 | 10 | 8 | 7 | 17 | 4.4 | 5.3 | 5.5 | 5.5 |
| C. striatus 978 | 500 | 622 | 672 | 1596 | 4.7 | 4.6 | 4.6 | 4.6 |

| | MnP, U l$^{-1}$ (610 nm) | | | | MnP, U l$^{-1}$ (270 nm) | | | |
|---|---|---|---|---|---|---|---|---|
| | Cultivation days | | | | | | | |
| | 5 | 7 | 9 | 12 | 5 | 7 | 9 | 12 |
| C. unicolor 300 | 423 | 92 | 30 | 14 | 980 | 120 | 34 | 0 |
| C. unicolor 301 | 953 | 1122 | 760 | 808 | 2242 | 2761 | 705 | 1152 |
| C. unicolor 302 | 16 | 24 | 13 | 24 | 0 | 17 | 9 | 0 |
| C. unicolor 303 | 962 | 1072 | 313 | 22 | 2219 | 1376 | 237 | 56 |
| C. unicolor 305 | 843 | 935 | 911 | 513 | 1213 | 1084 | 714 | 731 |
| C. gallica 142 | 74 | 57 | 108 | 111 | 52 | 69 | 52 | 60 |
| M. tremelosus 206 | 11 | 25 | 58 | 0 | 0 | 17 | 34 | 0 |
| P. tuberculosus 121 | 701 | 898 | 591 | 124 | 0 | 22 | 0 | 0 |
| P. tuberculosus 131 | 846 | 363 | 400 | 347 | 26 | 26 | 86 | 26 |
| C. striatus 978 | 0 | 0 | 4 | 0 | 17 | 0 | 38 | 0 |

| | LiP, U l$^{-1}$ | | | |
|---|---|---|---|---|
| | Cultivation days | | | |
| | 5 | 7 | 9 | 12 |
| C. unicolor 300 | 47 | 98 | 196 | 0 |
| C. unicolor 301 | 1 | 37 | 67 | 110 |
| C. unicolor 302 | 6 | 74 | 103 | 0 |
| C. unicolor 303 | 24 | 35 | 59 | 5 |
| C. unicolor 305 | 47 | 73 | 25 | 70 |
| C. gallica 142 | 3 | 121 | 107 | 6 |
| M. tremelosus 206 | 0 | 0 | 0 | 0 |
| P. tuberculosus 121 | 0 | 0 | 0 | 0 |
| P. tuberculosus 131 | 47 | 0 | 0 | 2 |
| C. striatus 978 | 7 | 0 | 0 | 0 |

2. Alginate Encapsulation of Enzyme Cocktail

Mycoremediation Via Encapsulation and Controlled Release of Ligninolytic Enzymes from Alginate Microparticles The goal of this work is to develop the use of alginate encapsulation approaches for ligninolytic enzymes for the stabilization and controlled release in soils contaminated with target hydrocarbons. The ideal result will be the identification of the materials and methods yielding alginate microparticles meeting the following:
  Small enough size that they can be dispersed in aqueous medium and sprayed onto soil
  High active until loading (Units/mass of dispersion)
  Long term stability
  Demonstrated ability to degrade hydrocarbons in contaminated soil.

Task 1—Investigate the Effect of Mn2+ on Enzyme Activity in Alginate Beads

We will test the effect of the inclusion of Mn2+ on the encapsulation of three ligninolytic enzymes: lignin peroxidase (LiP), manganese-dependent peroxidase (MnP) and laccase. We will evaluate the capsules' size and enzyme loading. A promising formulation will be selected for investigation into methods to reduce the size.

Task 2—Investigate Methods of Reducing the Alginate Bead Size

Methods to be investigated are microemulsion and extrusion techniques. These methods will be evaluated based on particle size, dispersability, and potential sprayability. In addition, we will evaluate the enzyme loading in each microcapsule (units/mass capsule), The most promising method(s) will be chosen for testing long term stability and efficacy in contaminated soil.

Task 3—Stability and Efficacy

One or more promising methods will be chosen for final stability and efficacy tests. These will be tested against unencapsulated control enzymes. Results will be gauged on both the ability of the capsule to improve enzyme stability as well as ability to degrade the target hydrocarbons in contaminated soil.

TABLE 2

Experimental Test Matrix for Tasks 1 and 2. Alginate concentration will be constant at 20 mg/mL (2% w/v) based on prior results and published data. Enzyme loading will be chosen based on desired active units per mass of alginate.

| | | Compositional Variables Cross Link Density/Amendment | | | Method Extrusion, | Processing Variables | | |
|---|---|---|---|---|---|---|---|---|
| | | | | | | For Excursion | For Emulsion | |
| Task | Run (#) | $C_{BaCl2}$ (mM) | $C_{CaCl2}$ (mM) | $C_{MnCl2}$ (mg/mL) | Spray, Emulsion | Flow Rate (mL/hr) | Stir Rate (RPM) | $C_{Tween80}$ (mg/mL) |
| 1 | 1 | 0 | 10 | 100 | Extrusion | 10 | | |
|   | 2 | 1 | 0 | 100 | Extrusion | 10 | | |
| 2 | 3 | TBD | TBD | 100 | Extrusion | | 200 | 2 |
|   | 4 | TBD | TBD | 100 | Extrusion | | 400 | 2 |
|   | 41 | TBD | TBD | 100 | Extrusion | | 200 | 4 |

Encapsulation Experiments Continued

Background/Executive Summary

In the first round of alginate experiments, we saw that the conditions were not able to yield discrete alginate particles. The beads did not solidify and most of the collection bath became brown indicating that enzyme was not efficiently encapsulated. We hypothesized that the concentration of the crosslinking divalent ions were too low, and that this was resulting a weak encapsulating hydrogel matrix. To test this, we amended our test matrix to test three combinations of crosslinking divalent ions, each with higher concentrations of CaCl2 and BaCl2. The concentration of MnCl2 was kept constant at 100 mM since this is already high, and because the Mn2+ ion place a role in the enzyme activity in addition to crosslinking the alginate. The result confirmed our hypothesis and increasing the CaCl2 and BaCl2 concentrations yielded much more robust, and spherical beads. However, the collection bath still showed some brown color. We will run enzyme activity tests to quantify the units per bead. This will be done by dissolving a bead in 55 mM sodium citrate and running an assay on the solution. We will also run assays on the collection bath solutions.

Approach

Materials

A stock solution of Alginate in DI water was prepared at 40 mg/mL and dissolved by heating in an autoclave. Other stock solutions were prepared accordingly. ABTS (10 mg/mL), CaCl2 (200 mM), MnCl2 (200 mM) and BaCl2 (10 mM) in DI water. Enzyme (MnP from C, unicolor 300) was used as received. This was a vicious dark brown liquid with the following estimated enzyme concentrations: laccase (437 U/mL), MnPA270 (265 U/mL), yielding a total enzyme concentration of 840 U/mL.

Procedure

1. To a 20 mL glass scintillation vial, add:
   a. 3.3 mL Alginate Stock (40 mg/mL; via 10 mL B-D syringe and 18 gauge hypodermic
   b. 2.9 mL enzyme (MnP from C unicolor 300; via 10 mL B-D syringe and 18 gauge hypodermic
   c. 0.132 mL of ABTS (10 mg/mL in DI water; via volumetric pipette)
   d. 0.289 mL of DI water (via volumetric pipette)

2. This resulted in pre-alginate solution with the following concentrations:
   a. 365 U/mL total enzyme (composed of the following enzymes)
   b. 190 U/mL Laccase
   c. 115 U/mL MnPA610
   d. 60 U/mL MnPA610
   e. 0.2 mg/mL ABTS
   f. 20 mg/mL Alginate 3. This solution was dispensed into collection baths with various concentrations of crosslinking ions (shown in Table 1 below), including MnCl2, CaCL2. For each run, 1 mL of pre-alginate solution was dispensed (at 10 mL/hr) through a 22 gauge stainless steel, blunt tipped needle into 50 mL of crosslinking solution in the collection bath. As the droplets hit the solution, they immediately solidified and sank to the bottom of the dish. The dish was rotated by hand to avoid accumulation of beads in one place in the dish. Note, that throughout the dispensing step, the collection bath gradually adopted a light brown color, indicating that some of the enzyme was diffusing from the beads into the collection bath.

4. After 1 mL was dispensed, the dish was left to sit for at least 30 minutes to allow the crosslinking to complete. Then the liquid was pipetted off the stored as the decantate. The dry beads were imaged using a camera (images were later analyzed for particle diameter using ImageJ software). These were then resuspended in 1 mL of DI water and stored in the refrigerator.

Results

The two of the runs (samples 3 and 4) yielded discrete beads that were able to be measured using ImageJ. If we assume that all of the enzyme in the pre-alginate solution was encapsulated in the beads (i.e. 100% encapsulation efficiency), and we estimate the bead volume from the measured diameters, we can estimate the enzyme concentration per bead (U/bead). This is shown in the Table below. Images and particle size distributions are shown in Figure below.

TABLE 1

Bead size and Estimated Enzyme loadings for successful runs (3 and 4).

| Date (y/m/d) | Run (#) | $C_{BaCl2}$ (mM) | $C_{CaCl2}$ (mM) | $C_{MnCl2}$ (mg/mL) | Bead Diameter (mm) | Enzyme Loading (U/bead) | | |
|---|---|---|---|---|---|---|---|---|
| | | | | | | Laccase | $MnP_{270}$ | $MnP_{610}$ |
| 2015 Mar. 18 | 1 | 10 | 100 | 0 | NA | NA | NA | NA |
| 2015 Mar. 18 | 2 | 0 | 100 | 1 | NA | NA | NA | NA |
| 2015 Mar. 23 | 3 | 50 | 100 | 2.5 | 2.8 ± 0.1 | 2.18 | 1.32 | 0.690 |
| 2015 Mar. 23 | 4 | 100 | 100 | 0 | 3.0 ± 0.1 | 2.69 | 1.63 | 0.848 |
| 2015 Mar. 23 | 5 | 0 | 100 | 5 | NA | NA | NA | NA |

It looks like sample 3 had better encapsulation efficiency than 4. Although it could be improved. Most of the enzyme is being lost in the bath. There are three things we could try to improve the encapsulation efficiency.

(1) Test higher concentrations of crosslinkers (CaCl2, and BaCl2)
(2) Store the beads dry and then disperse them in water when we're ready to test
(3) Reduce the amount of time that the beads are sitting in the bath before collection Note: Encapsulation efficiency is based on enzyme activity assays. Thus, it is possible that there is some de-activation enzyme encapsulated that was not detected by the assay. This would mean that the actual encapsulation efficiency of the enzyme was higher by some unknown amount, and that this was effect by enzyme de-activation in the process.

The invention claimed is:

1. An encapsulated fungal enzyme composition in the form of beads, comprising:
an extracellular enzyme suite comprising at least two enzymes selected from manganese peroxidase, lignin peroxidase, or laccase;
and further comprising $Mn^{2+}$ ions or a peroxide; and
wherein the extracellular enzyme suite is encapsulated within a shell, wherein the shell comprises a first layer and a second layer, wherein the first layer is interfaced with the extracellular enzyme suite and wherein the first layer comprises a cross-linked hydrogel; and wherein the second layer is interfaced with the first layer and wherein the second layer comprises poly (lauryl methacrylate), poly(stearyl methacrylate), poly (isoprene), or poly(butadiene).

2. The composition of claim 1 wherein the cross-linked hydrogel comprises calcium alginate, manganese alginate, zirconium alginate, calcium poly(aspartate), manganese poly(aspartate) or zirconium poly (aspartate).

3. The composition of claim 1 wherein the cross-linked hydrogel exhibits one of more of the following properties: a biodegradable matrix, water absorption, VOC-free, solventless, variable particle size, or stable in a pH range of 4 to 6.

4. The composition of claim 1 wherein the enzyme suite is purified.

5. The composition of claim 1 wherein the cross-linked hydrogel includes a mediator that affects a catalytic function of the enzyme.

6. The composition of claim 5 wherein the mediator is a manganese material that activates a catalytic cycle of the enzyme.

7. The composition of claim 6 wherein the manganese material is a crosslinker for the cross-linked hydrogel.

8. The composition of claim 1 wherein the composition is in the form of a plurality of beads having an enzyme core encapsulated by the cross-linked hydrogel.

9. The composition of claim 8 wherein the beads have a diameter within a range of from about 1.5 mm to about 5 mm.

10. The composition of claim 1 additionally comprising a material combined with the encapsulated enzyme to enhance its performance in a specified application.

11. The composition of claim 10 wherein the material comprises a peroxide or a peroxide derivative.

* * * * *